United States Patent [19]

Forte et al.

[11] Patent Number: 4,531,517

[45] Date of Patent: Jul. 30, 1985

[54] EXTRACTOR FOR INTRAMEDULLARY FASTENERS

[76] Inventors: Thomas E. Forte, 1500 Oak Knoll Dr., Cincinnati, Ohio 45244; Ted K. Parr, 3069 W. Tower Ave., Cincinnati, Ohio 45238

[21] Appl. No.: 478,301

[22] Filed: Mar. 24, 1983

[51] Int. Cl.³ .............................................. A61F 5/04
[52] U.S. Cl. ............................ 128/92 EC; 128/92 R
[58] Field of Search ............ 128/92 E, 92 EC, 92 R, 128/303 R

[56] References Cited

U.S. PATENT DOCUMENTS 1,873,250  8/1932  Adolph .
2,631,584  3/1953  Purificato .
2,693,798  11/1954  Haboush .
2,951,282  9/1960  Albright .
3,120,700  2/1964  Chuplis, Jr. .
3,626,935  12/1971  Pollock et al. .

FOREIGN PATENT DOCUMENTS 735333  5/1943  Fed. Rep. of Germany ... 128/92 EC
814349  3/1981  U.S.S.R. ......................... 128/92 EC

*Primary Examiner*—C. Fred Rosenbaum
*Assistant Examiner*—C. W. Shedd
*Attorney, Agent, or Firm*—Wood, Herron & Evans

[57] ABSTRACT

An extractor for removing intramedullary fasteners such as Sampson rods and Rush rods from bone comprises a support including two spaced end plates connected by spreader rods, a carriage assembly having an engaging element adapted to engage one end of the intramedullary fastener and a threaded shaft connecting the support and carriage assembly and being adapted with the support to rotate and axially move the carriage assembly between the end sections of the support. The engaging element connects to the carriage assembly through a bearing element which prevents rotation of the engaging element, and in turn the intramedullary fastener, during the axial movement of the carriage assembly required to remove the fastener.

9 Claims, 2 Drawing Figures

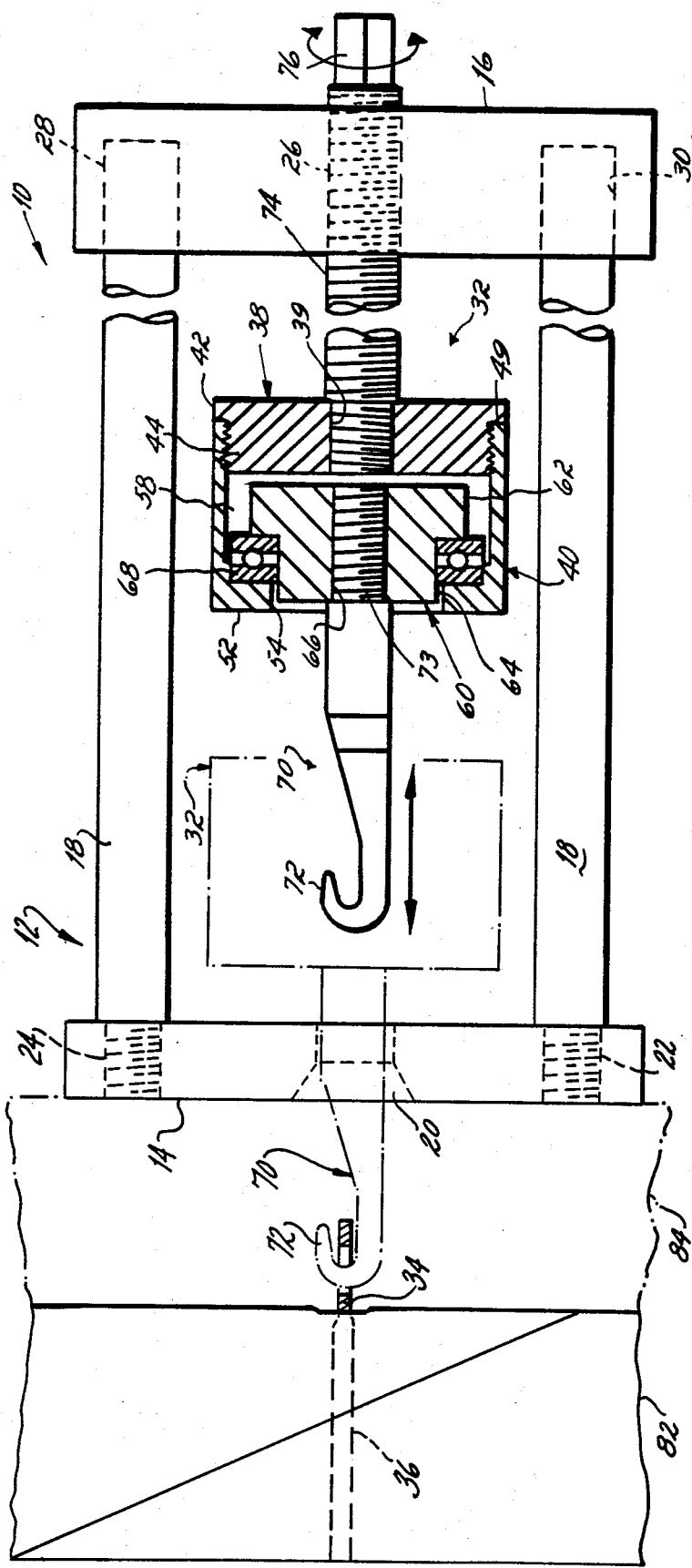
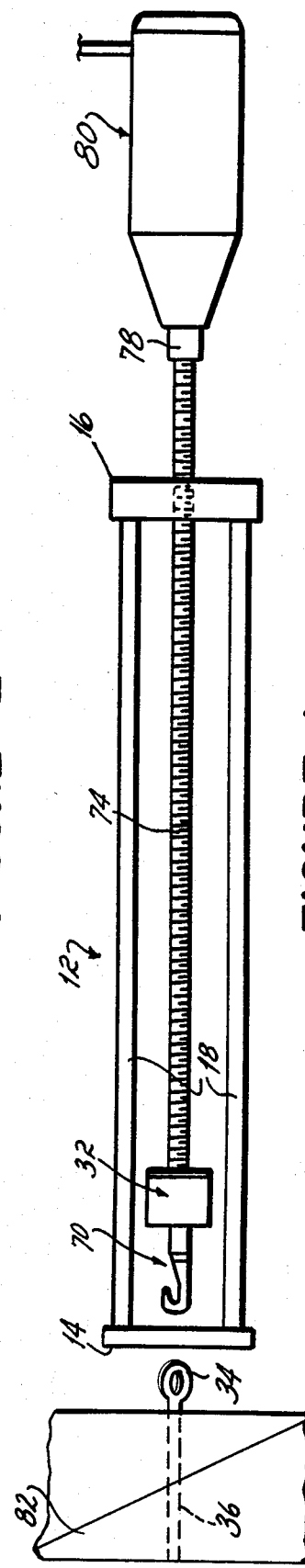
FIGURE 2
FIGURE 1

EXTRACTOR FOR INTRAMEDULLARY FASTENERS

FIELD OF THE INVENTION

This invention relates to the field of surgical instruments, and more particularly, to a device for extracting surgical pins and rods from bones of the body.

BACKGROUND OF THE INVENTION

Intramedullary fasteners such as Sampson rods and Rush rods are used to stabilize the location of bone fragments so that they may be closely approximated and placed in the proper anatomical position for healing. Particularly in younger patients, such fasteners are usually removed after the bone is fully healed. In other patients, removal may become necessary due to infection or pain caused by the fasteners, or in the event the fasteners become bent or fractured during rehabilitation.

Over a period of time, a fibrous band of bone marrow, tissue, and in some instances cancellous bone, grows around intramedullary fasteners making them difficult to remove. Preferably, the fasteners should be withdrawn from the bone along the axis in which they entered to avoid bending of the fastener and possible fracture of the bone. It is also desirable to avoid rotating the fastener during removal since such twisting motion can result in bending or fracture of the fastener in situ and/or damage to the bone.

Currently, intramedullary fasteners such as Sampson rods and Rush rods are most commonly removed by surgical pliers and other hand tools. In many instances, manual retraction procedures require a substantial amount of manual force and can be very time consuming and physically exhausting to the surgeon. Mechanical devices have been developed for the extraction of intramedullary fasteners, but for various reasons none have been considered an acceptable replacement for hand tools. The extractors disclosed in U.S. Pat. Nos. 2,693,798 and 3,626,935, for example, are relatively complicated in design and uneconomical. A comparatively simpler and cheaper device is described in U.S. Pat. No. 2,631,584, but that extractor causes the intramedullary fastener or rod to rotate as it is being withdrawn and also imposes an axial force directly against the bone and tissue surrounding the surgical fastener. This force can damage the tissue and cause the bone to chip or fracture. A further limitation of these prior extractors is that their fastener engaging ends or hooks are intended for a specific type of rod or nail and may not be interchanged to accommodate different types of fasteners or fasteners of varying sizes.

SUMMARY OF THE INVENTION

It is therefore among the primary objects of this invention to provide an intramedullary fastener extracting device which is of relatively simple, economical construction and is adapted to withdraw various types and sizes of surgical fasteners from bone without rotating the fastener and while distributing the axial pulling force required to remove the fastener over a relatively large area of bone and tissue surrounding the fastener.

The extractor comprises a support including spaced, front and rear end plates connected together by at least two spreader rods. Axially movable between the front and rear plates is a carriage assembly consisting of a body portion within which a mounting element is disposed and mounted on a bearing. A removable hook element is connected to the mounting element and is formed with a curved end adapted to engage the head portion of a surgical fastener. The support and carriage assembly are connected by a rotatable puller element which is adapted to first move the carriage assembly axially so as to place the curved end of the hook element into engagement with an end of the surgical fastener, and then move it in the opposite direction for removal of the fastener.

Due to the connection of the mounting element to the body portion of the carriage assembly by means of a bearing, the mounting element, and in turn the hook element, are prevented from rotating with the body portion and puller element as the entire carriage assembly is moved axially to remove the fastener. In this manner, the hook element exerts an axial force on the fastener without rotation or twisting. In addition, the forward plate of the support is shaped to engage a relatively large area of bone and tissue surrounding the fastener so as to better distribute the axial pulling force imposed by the support to avoid damage to the bone and tissue immediately adjacent the fastener.

DESCRIPTION OF THE DRAWINGS

The structure, operation and advantages of this invention will become further apparent upon consideration of the following description taken in conjunction with the accompanying drawings wherein:

FIG. 1 is a diagrammatic side view of the extractor for removing fasteners according to this invention; and FIG. 2 is a side view in partial cross section of the extractor shown in FIG. 1.

DETAILED DESCRIPTION OF THE INVENTION

Referring now to the drawings, an intramedullary fastener extractor 10 according to this invention is illustrated. The extractor 10 includes a support 12 which comprises a front plate 14 and a rear plate 16 connected by a pair of spreader rods 18 having threaded ends. The front plate 14 is formed with a tapered central opening 20 disposed between a pair of threaded bores 22 and 24 which extend part way through the front plate 14 and are adapted to receive the threaded ends of rods 18. The rear plate 16 includes a central threaded bore 26 disposed between a pair of threaded bores 28 and 30 which extend part way through rear plate 16 and are adapted to receive the opposite threaded ends of rods 18. All elements of the support 12 are preferably formed of stainless steel, cobalt chrome or similar materials.

A carriage assembly 32 is provided which is adapted to engage the end 34 of an intramedullary fastener 36. A typical Sampson rod having an eyelet at the end 34 is illustrated in the Figures as the intramedullary fastener 36, but it should be understood that other fasteners including Rush rods and the like may be removed by the extractor 10 of this invention. The carriage assembly 32, preferably formed of stainless steel, includes a body portion consisting of a male section 38 and a female section 40 adapted to receive the male section 38. The male section 38 is generally T-shaped having a head 42, and a stem 44 formed with exterior threads. A threaded bore 39 extends through the center of male section 38 for purposes to become apparent below. The female section 40 is cup-shaped and includes threads formed on its interior surface which extend downwardly a short distance from its upper edge 49 and are adapted to engage the exterior threads of the male section 38. The body portion of carriage assembly 32 is assembled by threading male section 38 into female section 40 such that the upper edge 49 of the female section 40 seats against the underside of the head 42 of male section 38.

The base of female section 40 includes a radially inwardly extending, annular flange 52 in which a central opening 54 is formed. The annular flange 52 is spaced from the bottom of the stem 44 of male section 38 forming a cavity 58 therebetween. Disposed in the cavity 58 is a mounting element or hook mount 60 having a head section 62 and a stem section 64. The hook mount 60 is supported within the cavity 58 by the engagement of its head section 62 with the upper surface of a bearing 68 mounted to the annular flange 52 at the base of female section 40.

The body portion of the carriage assembly 32 is adapted to engage the fastener 36 by an engaging element in the form of a hook 70 having a curved end 72 formed to engage the end 34 of the fastener 36, and a threaded end 73 engageable with a threaded, through bore 66 formed in the hook mount 60. While the hook element 70 is shown in the drawings with a curved end 72, this is but one configuration and size contemplated herein. An advantage of this invention over prior art extractor devices is that hook element 70 may be threaded out of the hook mount 60 and replaced by another hook element 70 having a different configuration or size depending on the size and type of fastener 36 to be removed. The replacement of hook element 70 is accomplished by unthreading male section 38 from the female section 40 and removing the hook mount 60 and hook element 70 from the cavity 58. The existing hook element 70 is then unthreaded from the hook mount 60 and replaced by another. It is contemplated that this procedure could be quickly and easily done by the attending physician either before or during the operation once these elements are removed from a sterilization device.

The support 12 and carriage assembly 32 are connected by a puller element in the form of a rod or shaft 74 which is threaded along its entire length. One end of the shaft 74 is threaded within the central, threaded bore 39 formed in the male section 38 of the body portion of carriage assembly 32. The remainder of shaft 74 is adapted to threadedly engage the central threaded bore 26 formed in the rear plate 16 of support 12. Rotation of shaft 74 results in axial movement of the shaft 74, and, in turn, carriage assembly 32, between the front and rear plates 14, 16. The end of shaft 74 adjacent the rear plate 16 of support 12 is formed with flats 76 adapted to receive the chuck or socket 78 of a power tool 80 or hand wrench (not shown) for effecting such rotation and axial movement of the shaft 74 and carriage assembly 32. It is contemplated that an electrically or pneumatically operated power tool 80 would be suitable for use as a means of rotating shaft 74.

In use, the intramedullary fastener extractor 10 of this invention operates as follows. The shaft 74 is first rotated clockwise to advance the carriage assembly 32 axially toward the front plate 14 so that the curved end 72 of hook element 70 extends through the tapered central opening 20 in front plate 14 and into engagement with the end 34 of the intramedullary fastener 36. In this direction of rotation, no axial forces are imposed on the extractor 10 and thus the entire carriage assembly 32 both rotates with the shaft 74 and moves axially toward the front plate 14.

Once the curved end 72 of hook element 70 is placed in engagement with the fastener 36, the shaft 74 is rotated in the opposite, counterclockwise direction. An axial force is applied to the fastener 36 urging it outwardly from the bone 82, and an equal and opposite force is applied by front plate 14 to the patient's body 84. It is advantageous to provide a front plate 14 having a relatively large surface area to distribute the axial pulling force over a correspondingly large area of the body 84. In one embodiment of this invention, the front plate is approximately 3 inches long and 1½ inches wide. This reduces potential damage to the bone 82 and possible necrosis which may result from pinched blood vessels and crushed tissue immediately surrounding the fastener 36. In addition, the tapered shape of the central opening 20 of front plate 14 tends to distribute the axial pulling force applied directly to the bone over a relatively large surface area to avoid chipping of the bone.

As mentioned above, current apparatus used to remove intramedullary fasteners, including hand tools or mechanical devices, generally twist or rotate the fasteners as they are withdrawn from the bone. Such twisting movement can snap the fasteners in two or in some cases create a new fracture of the bone. An important aspect of this invention is that the hook element 70 which engages the intramedullary fastener 36 is inhibited from rotating while moving in the axial direction to remove the fastener 36. This is accomplished by the connection of the hook mount 60, which supports hook element 70, to the bearing 68. Axial pulling force required to remove the fastener 36, which is applied as the shaft 74 rotates, is transmitted from the shaft 74 to the male and female sections 38, 40 of carriage assembly 32 and then through bearing 68 to the hook mount 60 and hook element 70. All elements of the carriage assembly 32, as well as the hook mount 60 and hook element 70, move axially with the shaft 74. The male and female sections 38, 40 of the carriage assembly 32 rotate with the shaft 74. However, the bearing 68 connecting the female section 40 to hook mount 60 allows the hook mount 60 to remain stationary relative to the rotating female section 40. In turn, the hook element 70 connected to the hook mount 60 also remains rotatably stationary relative to female section 40 but movable axially with the remainder of carriage assembly 32. Therefore, the intramedullary fastener 36 is subjected to primarily an axial force during the removal operation.

While the invention has been described with reference to a preferred embodiment, it will be understood by those skilled in the art that various changes may be made and equivalents may be substituted for elements thereof without departing from the scope of the invention. Therefore, it is intended that the invention not be limited to the particular embodiment disclosed as the best mode contemplated for carrying out this invention, but that the invention will include all embodiments falling within the scope of the appended claims.

What is claimed is:

1. Apparatus for extracting a bone fastener from a bone of a patient comprising:

a support having an end adapted to engage the patient;

a threaded rod connected to said support, said threaded rod being axially movable relative to said support upon rotation of said threaded rod;

a carriage assembly connected to said threaded rod, said carriage assembly being rotatable and axially movable with said threaded rod toward and away from the patient;

an engaging element adapted to connect to said bone fastener; and means for nonrotatably mounting said engaging element to said carriage assembly, said engaging element being movable axially with said carriage assembly and said threaded rod for extracting said bone fastener from the patient.

2. The apparatus of claim 1 in which said carriage assembly includes a body portion, said means for nonrotatably mounting said engaging element to said carriage assembly comprising a mounting element, and a bearing for mounting said mounting element to said body portion, said engaging element being connected to said mounting element.

3. Apparatus as in claim 1 in which said support includes front and rear end plates connected by at least two rods, said front plate being formed with a tapered central opening and said rear plate being formed with a threaded through bore, said front plate being adapted to engage the patient.

4. Apparatus as in claim 3 in which said threaded rod is adapted to threadedly engage said through bore of said rear plate of said support, said threaded rod being rotatable to move said carriage assembly axially between said front and rear plates of said support.

5. Apparatus as in claim 1 in which said carriage assembly includes a body portion having a male section threadedly engageable within a hollow, female section forming a cavity therebetween, said male section being formed with a threaded, through bore, said female section having a base including an internal annular flange formed with a central bore.

6. Apparatus as in claim 1 in which one end of said threaded rod is formed with flats adapted to engage means for rotating said threaded rod.

7. Apparatus for extracting a bone fastener from a bone of a patient comprising:

a support having spaced front and rear end sections, said front end section being adapted to engage the patient and said rear end section being formed with a threaded bore;

a carriage assembly including:
  a rotatable body portion;
  a bearing attached within said body portion;
  a mounting element mounted to said bearing, said bearing being adapted to nonrotatably mount said body portion to said mounting element;
  a hook element having one end adapted to engage said bone fastener and the other end connected to said mounting element;

a threaded rod connecting said support and said carriage assembly, said threaded rod being connected at one end to said carriage assembly, the other end of said threaded rod being rotatable within said threaded bore of said rear end section of said support for axial movement of said threaded rod relative to said support, said threaded rod being rotatable to apply an axial force to said carriage assembly for removal of said bone fastener from said bone, said body portion of said carriage assembly being rotated with said threaded rod while said mounting element and hook element remain nonrotatable relative to said body portion and threaded rod.

8. Apparatus for extracting a bone fastener from a bone of a patient comprising:

a support having spaced front and rear end sections, said front end section being adapted to engage the patient and said rear end section being formed with a threaded bore;

a carriage assembly including:
  a rotatable body portion;
  a bearing attached within said body portion;
  a mounting element mounted to said bearing, said bearing being adapted to nonrotatably mount said body portion to said mounting element;
  a hook element having one end adapted to engage said bone fastener and the other end connected to said mounting element;

a threaded rod connecting said support and said carriage assembly, said threaded rod being connected at one end to said carriage assembly, the other end of said threaded rod being rotatable within said threaded bore of said rear end section of said support for axial movement of said threaded rod relative to said support; and means adapted to rotate said threaded rod for applying an axial force to said carriage assembly for removal of said bone fastener from said bone, said body portion of said carriage assembly being rotated with said threaded rod while said mounting element and said hook element remain nonrotatable relative to said body portion and said threaded rod.

9. Apparatus as in claim 8 in which said means for rotating said threaded rod is a power tool having a chuck, said chuck being adapted to engage flats formed on said threaded rod.

* * * * *